United States Patent [19]

Graveno

[11] 4,185,328
[45] Jan. 29, 1980

[54] SIGHT AND VISION PROTECTION FOR ARC WELDING HELMET

[76] Inventor: John C. Graveno, 1114 Winston Rd., So. Euclid, Ohio

[21] Appl. No.: 759,621

[22] Filed: Jan. 17, 1977

[51] Int. Cl.$^2$ ............................................. A42B 1/00
[52] U.S. Cl. ............................................................ 2/8
[58] Field of Search ........................... 2/10, 8, 431, 432

[56] References Cited

U.S. PATENT DOCUMENTS

| | | | |
|---|---|---|---|
| 1,205,308 | 11/1916 | Work | 2/8 |
| 2,363,461 | 11/1944 | Huntsman | 2/8 |
| 3,267,807 | 8/1966 | Snope et al. | 2/432 |
| 3,868,726 | 3/1975 | La Marre et al. | 2/8 |

Primary Examiner—Doris L. Troutman

[57] ABSTRACT

An improved arc welder's helmet and window assembly for protecting the welder's face and eyes from sparks and flying particles and also from visual and other radiation emitted from his own work and from other sources about and behind the helmet. The helmet is conventional and has a cylindrical forward face curved about its vertical axis, and is preferably made of rigid, light and spark-proof construction and material with a conventional rectangular forward opening covered by a window assembly including a darkened pane or so-called lens. The window assembly comprises a conventional forwardly disposed first frame part on the outside of the helmet with a concave, rectangular, perimetric flange bearing on the front face of the helmet all around the window opening, and also comprises a rearwardly disposed second frame part on the inside of the helmet with a complementary, convex, perimetric flange adapted to bear on the interior surface of the helmet all around the said window opening. A backlight mask or guard has novel coaction with the helmet, window and welder and has a convex, rectangular flange at its forward end which is of substantially the same size and form as the flange on the said second frame part and is disposed and squeezed perimetrically around said opening between the interior surface of the helmet and the flange of second frame part when said frame parts are clamped together tightly. The backlight guard is hollow, yielding and opaque, and it extends rearwardly and tapers outwardly from the window opening to fit comfortably and closely with the brow, temples, nose and face of the welder and excludes all light and other radiation from reaching the rearward surface of the window and being reflected toward the eyes of the welder. The guard and second frame part may be bonded together and/or made for use as a unit.

11 Claims, 6 Drawing Figures

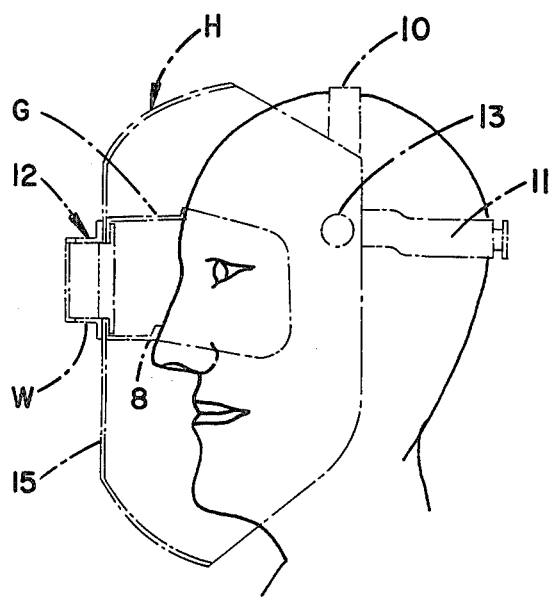
FIG. 1
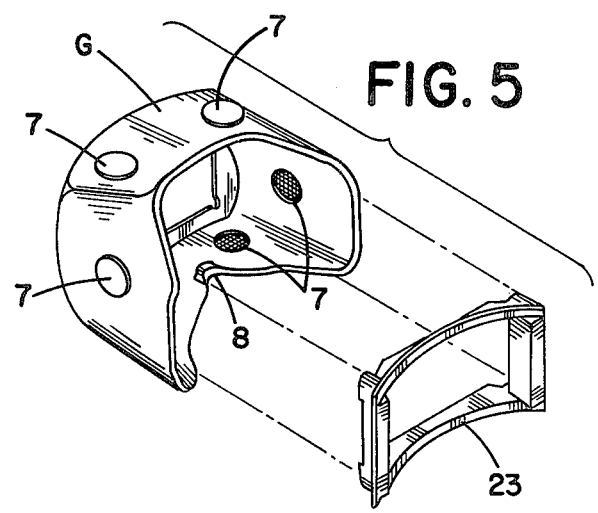
FIG. 5
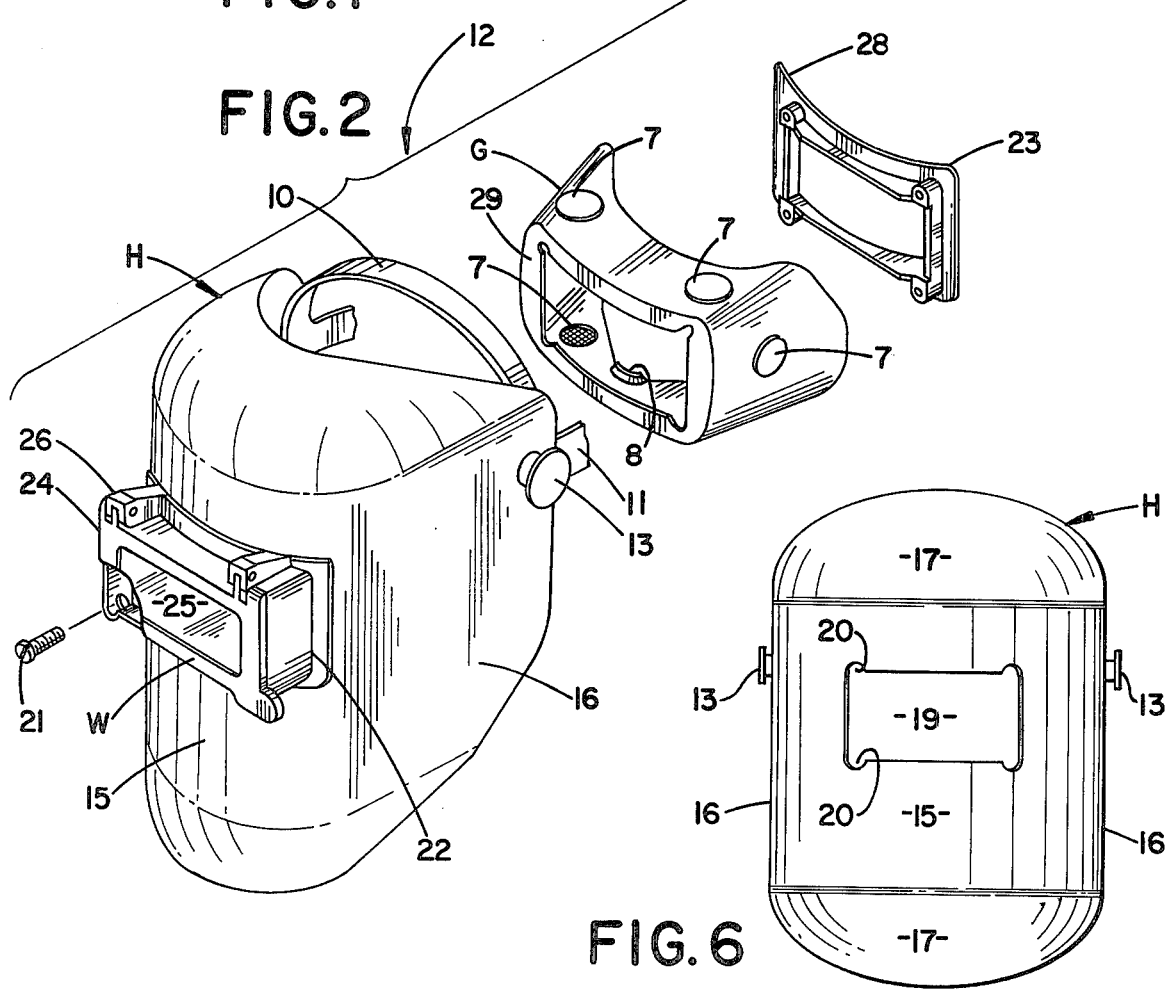
FIG. 2
FIG. 6

SIGHT AND VISION PROTECTION FOR ARC WELDING HELMET

BACKGROUND OF THE INVENTION

Arc welders wearing conventional safety helmets with a protective darkened window frequently experience considerable injury to their eyes and experience difficulty in viewing the work. I have discovered that this difficulty is due largely to the reflected glare from the inside surface of the protective and/or darkened window by reflected light or other radiation that reaches the window from the welder's side of the window around the inner sides and under the top of the helmet. Such light and radiation is emitted from surrounding areas adjacent and behind the welder and his work. Such other sources of radiation are welding arcs that have been struck by other welders in the vicinity, essentially rightwardly or leftwardly behind the welder, and even indirectly from the welder's own arc.

When the welder has a conventional safety helmet in operating position over his face, there is necessarily a clearance of about an inch or more between the welder's head and the inside and rearward edges of the helmet. It is through this open space that the light and/or other radiation often enters and reflects off the inside surface of the lens or window to interfere with the welder's vision and/or his ability to view his work properly.

Gas welders usually employ no helmet and avoid the problem of reflection by wearing conventional gas-welding goggles with a soft flexible body portion that fits around his eyes. The problem with goggles, however, is that they are insufficient for use in arc welding operations, since not only the eyes, but also the entire face and neck of the welder must be protected from sparks and radiation.

The protective arc welder's helmet combined with my present invention, however, reduces the dangers and difficulties indicated above and affords other features and advantages heretofore not obtainable as will appear more fully below.

SUMMARY OF THE INVENTION

It is among the objects of my invention to protect an arc welder's face and eyes from not only sparks and radiation emitted from his own work, but also from the intrusion of light and other deleterious radiation from surrounding areas adjacent the welder that reflect off of the inside surface of the front window and/or darkened lens through which the welder must see his work.

Another object is to construct an arc welder's helmet with a "back-light" guard that affords improved viewing capability for the welder, helps him see his work and also affords novel protection of the welder's face, neck and eyes.

Another object is to prevent injury to the arc welder's eyes and prevent temporary or permanent impairment of his vision.

Another object is to provide "back-light" guards per se which welders may incorporate in arc welding helmets which lack them in the first instance, or for use in replacement or repair of worn or injured guards.

These and other objects and advantages will appear more fully below.

The combination to which my improvement pertains, includes a rigid, thin-walled helmet body with a curved front portion in front of the welder's face and which has a window with a darkened lens through which the welder can view the work when wearing the helmet. The window has a perimetric frame with separate parts, including one part inside the helmet and another part outside the helmet, both adjacent the peripheral edge of the aperture through which the welder views the work. The inner part has a smooth cylindrical convex perimetric flange engageable with the inside of the helmet around the perimetric zone adjacent the aperture. The outside part has a concave flange complementary to the convex flange of the inside part which engages the helmet opposite the engagement of the flange of the inside part.

In accordance with my improvement, the helmet and window assembly includes the back-light guard inside the helmet which fits easily against the front and sides of the welder's face to prevent light entering from the sides and rear of the helmet from reaching the interior surface of the darkened lens. The light guard has a forwardly disposed, convex curved perimetric flange which cooperates with the inner part of the window frame and which is clamped between the inner surface of the helmet and the inside part of the frame to secure the light guard in position, substantially integrated with the other parts of the helmet and window frame.

BRIEF DESCRIPTION OF THE DRAWINGS

FIG. 1 is a side elevation suggesting a welder's head with a phantom view of a welder's helmet assembly embodying my invention as suggested in vertical section in broken dash lines as worn by a welder in front of his eyes and about the welder's head and face.

FIG. 2 is an exploded perspective view illustrating the component parts of the assembly of window, window frame parts, helmet and guard embodying the invention.

FIG. 5 is a partial exploded perspective view taken from the left rear of the back-light guard or mask and the detached inner second frame part of the helmet assembly of FIGS. 2 through 4, and FIG. 6 is a front elevation of the helmet of FIGS. 2-4 showing the front opening unobscured by the exterior components of the window and window frame assembly.

DESCRIPTION OF THE PREFERRED EMBODIMENTS

Figure 4:
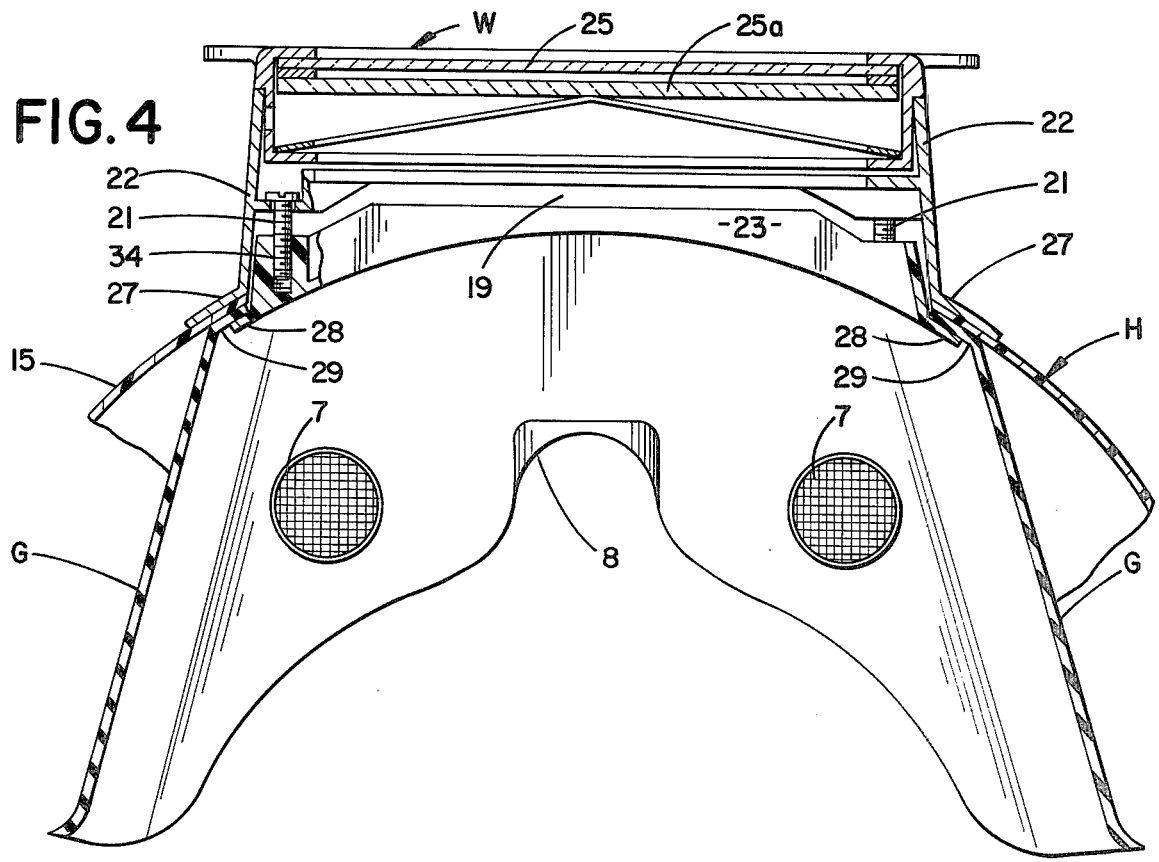
FIG. 4 is a fragmentary horizontal sectional view taken along the line 4—4 of FIG. 3.

Referring to FIG. 1 of the drawings, there is shown the welder's head, viewed from the side and with an arc welding helmet H and window assembly W and back-light guard G shown in phantom, broken dash lines and positioned before and about the welder's face and eyes. As shown best in FIG. 1, the bottom wall of guard G is notched at 8, FIGS. 1, 2, 4 and 5 to accommodate the welder's nose and permit him to breathe freely from below the guard. Conventional ventilating air filters 7 are secured in the walls of the guard G to provide fresh dry air within the guard and on the window. FIGS. 2, 4 and 5.

The helmet is adjustably supported on the head conventionally by top strap 10 and back strap 11 with conventional means for adjusting the straps to fit the welder's head. The helmet assembly 12 comprising helmet H, window assembly W and guard G is pivotable up and back from its position shown in FIG. 1 to a raised position (not shown) about pivots 13.

The conventional helmet H, FIGS. 2, 3, 4 and 6 comprises a vertical front, forward semi-cylindrical portion 15, curved about a vertical axis merging with parallel, rearwardly extending flat sides 16 and with upwardly and rearwardly curving upper, and downwardly curving lower, portions, 17. At about the welder's eye level, and opposite his eyes and nose, an opening 19, FIG. 6 is provided in the front portion 15. The opening is rectangular as enscribed on the cylindrical surface 15 with long parallel cylindrical, horizontal upper and lower sides and with short, straight vertical ends; the corners 20 of the opening being enlarged to accommodate clamp screws 21, FIGS. 2 and 4. The helmet is preferably made of light, strong, thin-walled, molded, fiberglass-reinforced, fire-resistant plastic, the interior of which is comfortably larger than and freely spaced from the welder's head and face.

The protective window lens assembly W includes an outer perimetric frame part 22 and a cooperating inner perimetric frame part 23, FIGS. 2-5, both of which are adapted to be fastened together surrounding the rectangular aperture 19 and supporting the guard G behind the opening. The outer frame 22 has a conventional lens holder 24 pivotally attached thereto and which carries a darkened lens 25 through which the welder views the work and which filters out most all the evil light radiation emitted from the work. The lens holder 24 is pivotally connected to the frame 22 at hinges 26 so that the darkened lens 25 may be swung upwardly out of the way.

Figure 3:
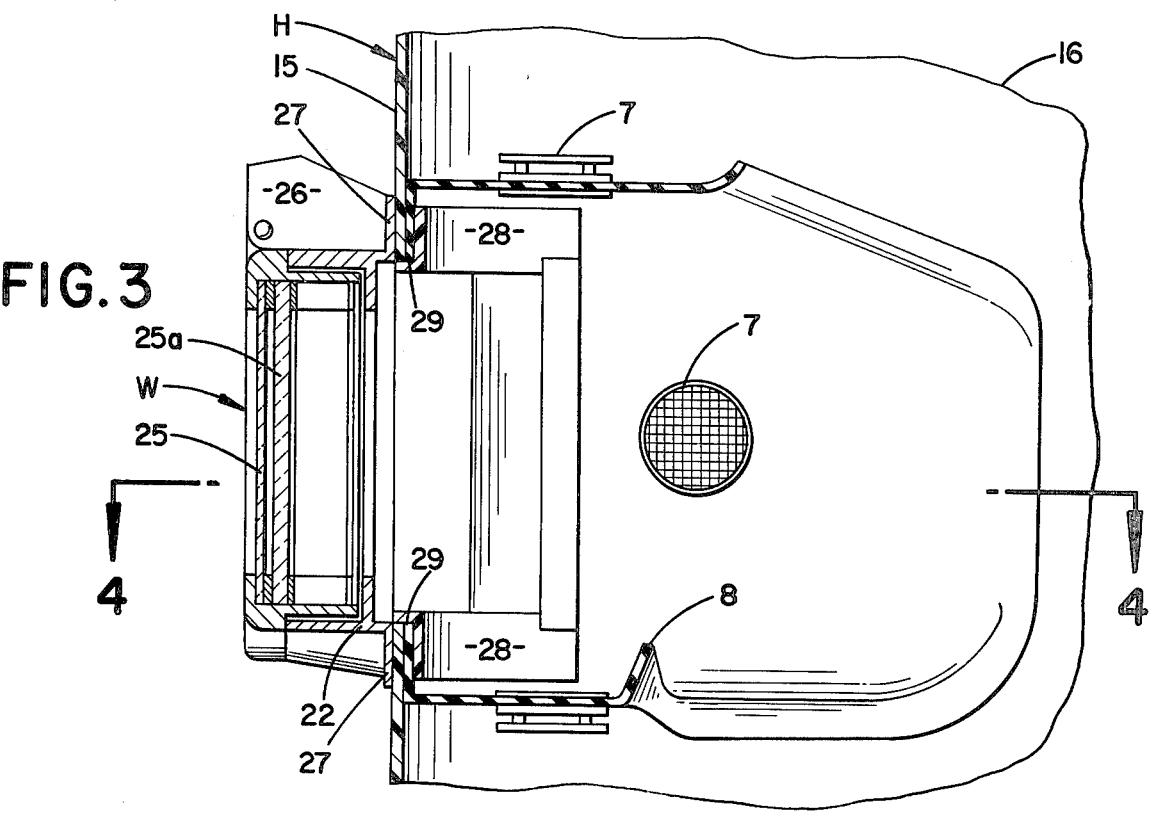
FIG. 3 is a fragmentary vertical section on an enlarged scale (approximately actual size) taken through the center of the helmet of FIG. 2 when all the parts are assembled.

As shown in FIGS. 3 and 4, a second window pane or darkened lens 25a is shown in addition to the lens 25 so that the darkness or lightness of the window may be selectively altered by choosing lenses or combining them.

The outer frame part 22, FIGS. 2, 3 and 4 has a concave, curved, perimetric flange 27 adapted to match the contour of the front portion 15 of the helmet and fit against the part of it surrounding the opening 19. The inner frame part 23 has a curved, convex, perimetric flange 28 formed to match the curve of the inner surface of the portion 15 surrounding the opening 19.

The light-guard or mask G is formed of soft, flexible, opaque, rubber-like material, such as vinyl, which opens rearwardly, FIGS. 1-5, to engage the contour of the welder's face nose, brow and temples all around his eyes. The guard thus prevents light and/or other radiation from reaching the welder's side of the window and reflecting back into his eyes. Referring to FIGS. 2, 3, 4 and 5, the forward end of the guard G comprises an inwardly turned, convex flange 29 having the same form and size as the flange 28 of inner frame part 23. Flange 29 is adapted to seat against the inner surface of portion 15 of the helmet on the marginal portion thereof surrounding the aperture 19, FIGS. 2-5. Flange 29 is firmly clamped in position through cooperation between flange 28 of inner frame part 23 and flange 29 of the outer frame part 22 of the viewing lens assembly W. The inner frame part 23 having been inserted through the inside of the guard G, FIGS. 2 and 5, and its flange portion 28 is pressed against the inside of flange 29 of the guard G.

With the parts in this assembled position, FIG. 1, screws 21, FIGS. 2 and 4, are passed through openings in the outer frame part 22 and into tapped holes 34 formed in the inner frame part 23. By tightening the screws 21, the respective parts are tightly clamped together in assembled operative condition for use by the welder as shown in FIGS. 1, 3 and 4.

My improvement protects the eyes of the welder and enhances his view of the work. It also provides sufficient space in front of his eyes to permit the welder to wear corrective spectacles. The softness of the guard G permits its comfortable light-proof contact with the welder's face and encourages its protective use.

While the rubber-like guard G has been illustrated and described specifically as an element separate from the inner window frame part 23, it has also been noticed that the guard and the frame part could be integrated for convenience in making my improved helmet as well as for convenient replacement and repair. For example, a simple adhesive or vulcanized bond between the convex forward face of the outwardly extending flange 28 of the inner frame part 23, see FIG. 2, with the concave inwardly extending rearward face of the flange 29 of the guard G would integrate those parts into one unitary working element.

While my invention has been shown and described herein with reference to a specific preferred embodiment thereof, this is intended for illustration rather than limitation. Modifications of and improvements on the specific device herein shown and described will occur to those skilled in the art without departing from the teaching and principles of my invention. Therefore I do not want my patent to be limited to the specific embodiment herein shown and described, nor in any way inconsistent with the progress in the art which has been promoted by my invention.

I claim:

1. The combination of an arc welder's helmet having a forwardly disposed protective window through which the welder views his work and from the welder's side of which back-light from within the helmet tends to reflect into the welder's eyes and impair his vision, and a hollow, back-light guard with opaque sides and open at both ends and disposed within the helmet between the window and the welder's face and preventing back-light from shining on the welder's side of the window and being reflected toward the welder's eyes.

2. The combination of claim 1 wherein said guard is soft and flexible for gentle, snug engagement with the welder's brow and nose, temples and face at its rearward open end, and said window has a frame engaging the open front end of said guard adjacent the window.

3. The combination of claim 1 wherein said window has a frame, one part of which is integrated with the open end of said guard adjacent the window.

4. The combination of an arc welder's helmet having a forwardly disposed protective window through which the welder views his work and from the welder's side of which back-light from within the helmet tends to reflect into the welder's eyes and impair his vision, and a hollow, back-light guard preventing such impairment with opaque sides open at both ends and disposed within the helmet between the window and the welder's face having light-proof engagement with the helmet adjacent the window and having light-proof engagement with the welder's face.

5. The combination of claim 3 wherein the window has a multi-part frame between parts of which the open front end of said guard and said helmet are engaged.

6. The combination of claim 5 wherein one part of said frame is permanently joined with the said open front end of said guard.

7. In the combination of an arc welder's helmet having a curved forward portion with an aperture and having a glazed window through which the welder can see the work when wearing the helmet with the window spaced horizontally from said aperture and the welder's eyes, the improvement comprising a frame for the window adjacent the periphery of said aperture and a light impervious guard disposed inside said helmet and engageable rearwardly with the brow and face of the welder to prevent light from reaching the interior surface of the window when the front of the guard has peripheral light-proof engagement with the helmet adjacent said aperture, and means for securing said frame and said guard to said helmet adjacent said aperture.

8. In the combination of an arc welder's helmet having a forward portion with an opening for a glazed window through which the welder can see the work when wearing the helmet with the window spaced from the welder's eyes, a frame around the window having separate parts disposed respectively inside and outside the helmet adjacent the periphery of said opening, said parts having perimetric surfaces engageable with the inside and outside of the forward portion of said helmet adjacent said opening, the improvement comprising a hollow back-light guard disposed and associated with said parts inside said helmet and engageable rearwardly with the front and sides of the face of the welder and having light-proof engagement with the inside of the helmet adjacent said opening, said guard preventing light from reaching the welder's side of said window when the helmet is worn by the welder, and means for securing at least one of said parts of said frame and said guard to said helmet adjacent said opening.

9. In the combination of an arc welder's helmet having a cylindrical vertical forward portion with an aperture for a chordal, planar window through which the welder can see the work and the welding arc when wearing the helmet with the window spaced horizontally from the welder's eyes, the improvement comprising a perimetric frame for the window having one part disposed outside the helmet adjacent the peripheral edge of said aperture and another part disposed inside the helmet adjacent the said edge of said aperture, both said parts having smooth cylindrical perimetric surfaces engageable with the said helmet upon limited areas perimetrically adjacent and surrounding said aperture, and a light guard disposed inside said helmet and engageable rearwardly with the front and sides of the face of the welder and adapted to prevent light from reaching the interior surface of the window when the front of the guard has light-proof engagement with the helmet adjacent said aperture, said guard having a forwardly disposed cylindrical, perimetric flange corresponding to the said cylindrical perimetric surface of said another part of said frame and adapted to be disposed between said another part of said frame and said helmet around said aperture, and means for clamping said parts of said frame and said flange of the guard to said helmet adjacent said aperture.

10. The improvement of claim 9 wherein the forward part of said guard and said another part of said frame are integrated into a single unitary element.

11. The improvement of claim 9 wherein the said flange of said guard is convex and turned inwardly and the flange of said another part of said frame is convex and turned outwardly and said another part of said frame is disposed within the front of the guard when the said flanges of the guard and said another part are in substantially coextensive engagement.

* * * * *